United States Patent [19]

Riccio

[11] 4,017,007
[45] Apr. 12, 1977

[54] SINGLE DOSE AIR PRESSURE OPERATED DISPENSER

[75] Inventor: Pasquale R. Riccio, Salem, N.H.

[73] Assignee: Ciba-Geigy Corporation, Ardsley, N.Y.

[22] Filed: June 24, 1975

[21] Appl. No.: 589,838

Related U.S. Application Data

[63] Continuation-in-part of Ser. No. 427,855, Dec. 26, 1973, abandoned.

[52] U.S. Cl. .............................. 222/80; 222/193; 222/325; 128/266
[51] Int. Cl.² ............... B05B 7/26; B65D 83/06; A61M 13/00
[58] Field of Search ............. 222/80, 193, 325; 239/309, 350, 355, 357; 169/33; 128/266

[56] References Cited

UNITED STATES PATENTS

| | | | |
|---|---|---|---|
| 1,989,715 | 2/1935 | Statham | 222/490 |
| 2,071,679 | 2/1937 | Bretschger | 222/490 X |
| 2,163,477 | 6/1939 | Warr et al. | 169/33 |
| 2,283,796 | 5/1942 | Darms | 169/33 |
| 2,301,718 | 11/1942 | Thorne | 169/33 |

FOREIGN PATENTS OR APPLICATIONS

| | | | |
|---|---|---|---|
| 532,513 | 2/1973 | Switzerland | 222/325 |
| 518,744 | 3/1970 | Switzerland | 222/325 |

Primary Examiner—Robert B. Reeves
Assistant Examiner—Frederick R. Handren
Attorney, Agent, or Firm—Wenderoth, Lind & Ponack

[57] ABSTRACT

An air pressure-operated dispenser for spraying a single dose of a fluent material of liquid or powder form. The dispenser has a single dose container having a compressed air inlet opening and a closable discharge orifice and means for closing the discharge orifice in a non-dispensing position of the dispenser. An air-compressing piston pump having a compressed air outlet from a compression space thereof is provided on the dispenser at the junction of the inlet opening and the compressed air outlet. The inlet opening of the single dose container is joined to the compressed air outlet of the compression space and valve means is provided on the piston pump for releasing a flow of compressed air after build up of a determined excess pressure.

9 Claims, 9 Drawing Figures

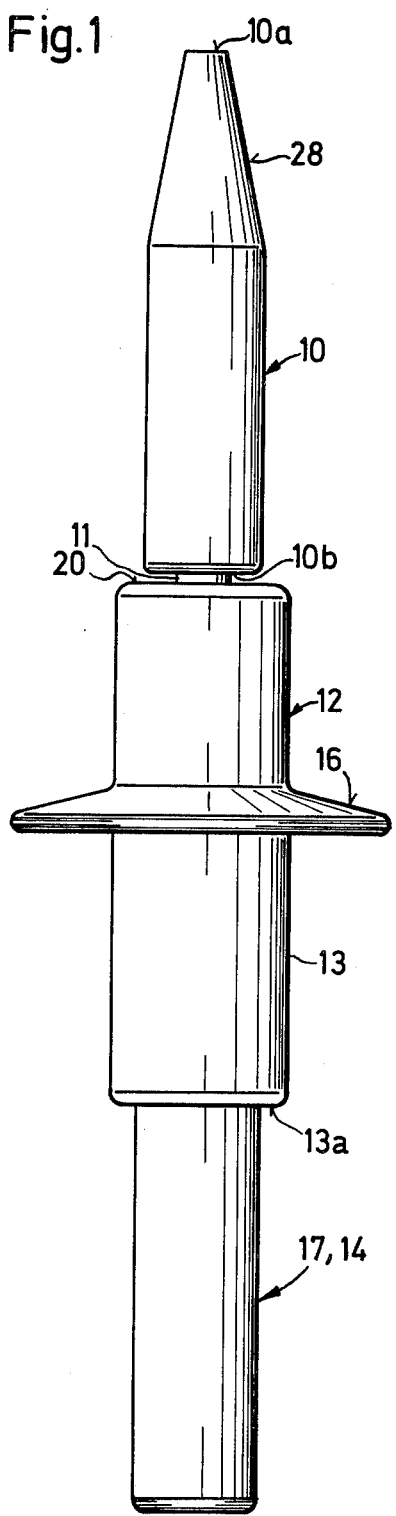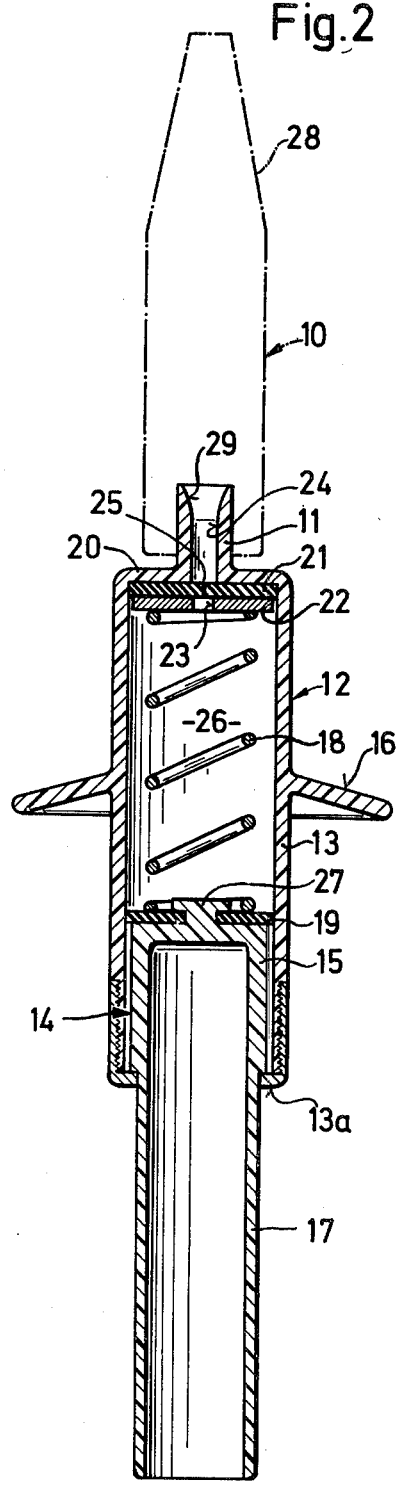

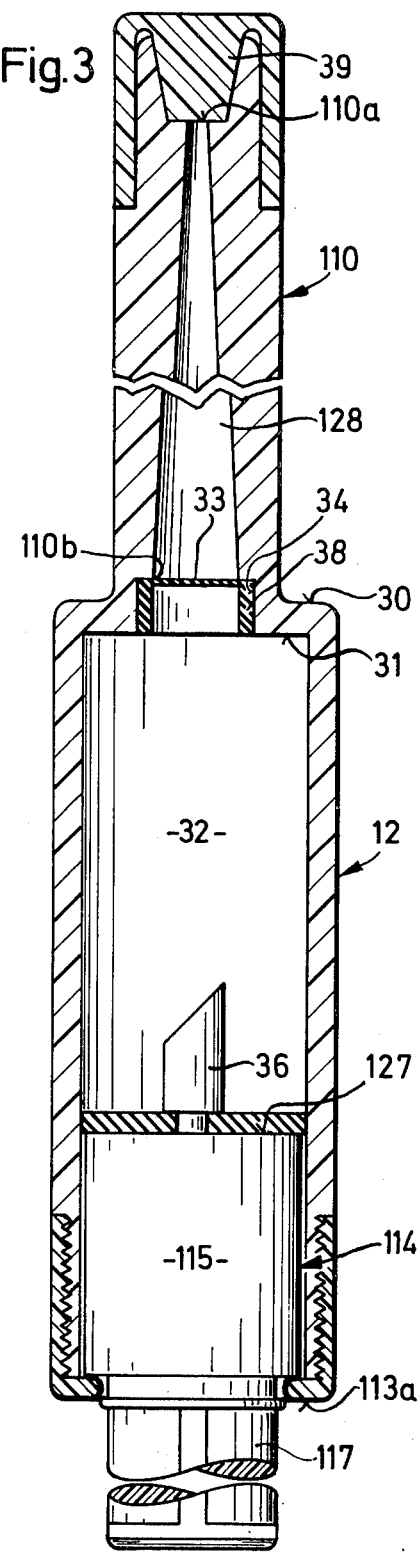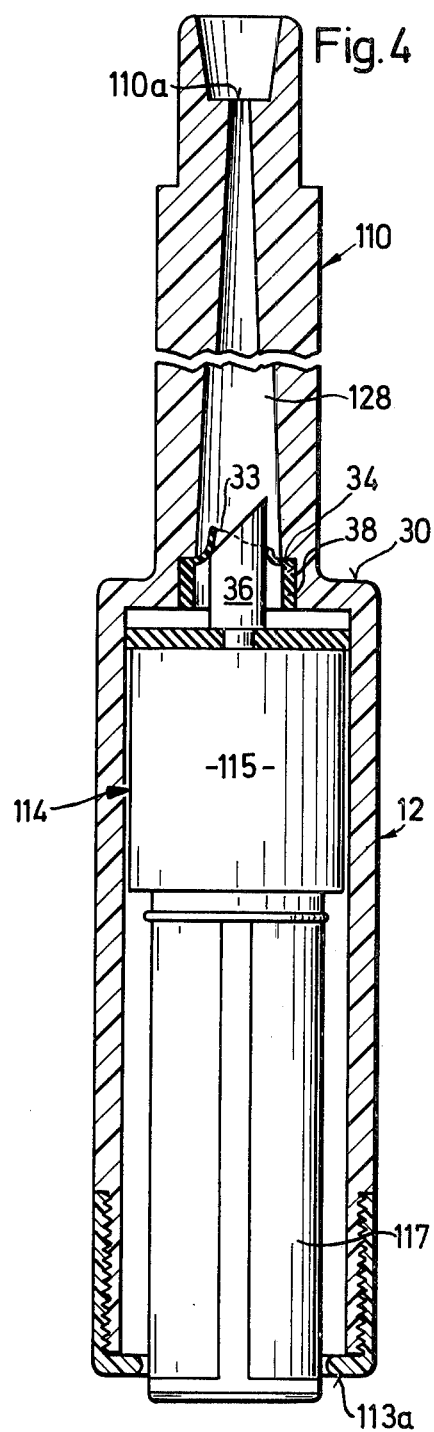

SINGLE DOSE AIR PRESSURE OPERATED DISPENSER

This application is a continuation-in-part of U.S. patent application Ser. No. 427,855 filed Dec. 26, 1973, now abandoned.

This invention relates to an air pressure-operated dispenser for spraying a single dose of a fluent material of liquid or powder form.

Known such dispensers comprise a single dose container having a compressed air inlet opening and a closable discharge orifice, means for closing the orifice in non-dispensing position of the dispenser, and an air-compressing piston pump having a compressed air outlet from a compression space thereof, the pump comprising valve means for releasing a flow of compressed air after build up of a determined excess pressure. "Fluent" materials usable in such dispensers are liquids or solid materials in powder form of sufficiently fine particle size to permit fluidization and spraying of the entire dose by the compressed air produced preferably by one compression stroke of the piston pump.

Dispensers are already known in which liquids and also powders may be dispensed in specific amounts from an aerosol container in which the liquids or powders are mixed with a gaseous propellant, such as highly halogenated lower alkanes (e.g. freons), butane/propane mixtures, carbon dioxide and/or nitrogen, by the opening of a dosing valve mounted on the container. A suitable dosing valve is described in German Pat. No. 1,149,300 (published 22.5.1963). Rubber balls and the like serving to produce a short puff of compressed air have also been used as propellant sources, e.g. in the device described in U.S. Pat. No. 2,519,555 concerning a dispenser for the dispensing of pulverulent medicaments.

With the older known devices, there is difficulty in obtaining an accurate dosage, particularly in the case of very small amounts extending, for example, down to a few milligrams, either because of the fact that the design of correspondingly small dosing valves with correspondingly accurate dimensioning and low tolerances is too complicated and expensive, or because of the fact that the complete removal of the stored amount of liquid from the dispenser and the transfer of this amount to the point of application cannot be guaranteed.

A device for the dispensing of liquid substances which is free from these drawbacks and which comprises a dispenser containing only the amount of liquid substance to be delivered in a single dose, and which can be connected to a propellant reservoir from which, on actuation of the dispenser, a gaseous propellant is forced through the dispenser to effect the fullest possible removal of the amount of liquid stored therein and the transfer of the ejected liquid to the desired point of application, is described in U.S. Pat. No. 3,739,951. The device there described comprises a casing having a dispensing outlet and an end face part having a propellant inlet opening therein, removable sealing means for the dispensing outlet and sealing means for the inlet opening, wherein the end face part is adapted to be attached to a propellant container, and a storage element which is contained in the casing and is connected with its one end to the dispensing outlet and with its other end to the inlet opening, and is destined for holding therein the specific dose of liquid to be dispensed, and wherein at least the portion of the storage element connected to the inlet opening is dimensioned to have a capillary effect on a liquid contained in the storage element so as to leave a gas pocket free between the liquid and the inlet opening, whereby a displacement of the liquid in the storage element is impeded when the dispensing device is shaken.

Such gas pockets are preferably provided at both open ends of the storage element. The propellant required for expelling the dose of liquid from the storage unit can compress air emitted from a bulb or flask of the type used in U.S. Pat. No. 2,519,555 or a similar air-compressing device.

This known device suffers from the drawback that it can only be used for liquid and not for powders, and moreover that the liquid must have an adequate viscosity and surface adhesion relative to wall of the capillary storage element.

On the other hand, powder dispensers ejecting a limited amount of powder with the air of compressed air are known, for instance, from U.S. Pat. No. 2,068,871, and other propellants such as carbon dioxide, fluorocarbon or hydrocarbon gases are used in devices described in U.S. Pat. Nos. 3,232,493 and 3,235,126. All of these devices require for operation fingers of only one hand of the user, while older devices have air pumps requiring handling by both hands of the user and do not permit discharge of exactly dosified amounts of powder or liquid. Exact dosification is also impossible in the device described in the above-mentioned U.S. Pat. No. 2,068,871 which requires fluidization of a large amount of powder in a powder storage chamber, only a small part of which is expelled from the discharge opening at one end of the storage chamber, while the air-compressing pump and a valve releasing compressed air into the interior of the comparatively large storage chamber are located at the other end of the chamber.

All of the above-described devices suffer or may suffer from the serious drawback that corners, recesses and dead angles may occur in the flow path of the product or product-propellant mixture in the product storage chamber and/or out of the mouth of the device, in which residual portions of liquid and particularly of fine powder may be retained so that the amount of product dispensed will be somewhat smaller than the prescribed dose, thus rendering exact dosification difficult or impossible.

Another drawback of all prior art devices resides in the difficulty of exactly matching the amount of propellant with the amount of fluent material to be dispensed.

Moreover, in the case of fluorocarbon or hydrocarbon propellants, a serious disadvantage may arise from the fact that these propellants are inhaled by the user, when medicaments are dispensed from the known inhaler devices using such propellants.

According to the present invention there is provided an air-pressure-operated dispenser for spraying a single dose of a fluent material of liquid or powder form, and comprising:

a. a single dose container having a compressed air inlet opening and a closable discharge orifice,
b. means for closing the discharge orifice in a non-dispensing position of the dispenser,
c. an air-compressing piston pump having a compressed air outlet from a compression space thereof, and
d. valve means for releasing a flow of compressed air after build up of a determined excess pressure, wherein the inlet opening of the single dose container is joined to the compressed air outlet of the compression space and wherein the valve means comprise an obturator located at the junction of the inlet opening and the compressed air outlet.

The present invention thus provides a single dose dispenser of the type using compressed air for the discharge which both preserves the advantages of the device described in U.S. Pat. No. 3,739,951 and permits dispensing of pulverulent solid as well as liquid materials. The dispenser of the invention does not depend on any capillary interaction between the fluent material and the walls of the product supply unit containing the same, and can be made as a simply constructed device which dispenses single doses of product with air compressed each time the device is actuated under the control of a simple and easily made valve means. All parts of the device are preferably simply molded in plastic; the product supply unit can be integral with the air-compression piston pump, or readily replaceable.

The device of the invention avoids the drawback of residual product left undispensed by ensuring that the air-compressing piston pump in the device releases the compressed air suddenly only after a maximum pressure has been attained. Naturally, the device should be so constructed that the pump delivers a sufficient amount of a compressed air and directs such compressed air in such manner toward the product dose that the entire mass of the latter is expelled from the device.

Preferably, the compressed air outlet has the same configuration as, and/or the same diameter as the inlet opening of the single dose container. The latter can either be mounted separately on the piston pump, or the single dose container and the piston pump can have a common hull. This hull can constitute the cylinder of the piston pump or the wall of the single dose container, or preferably both, the container and pump thus being integrated.

The interior space of the single dose container can be of frustoconical shape having its base open to constitute the compressed air inlet opening and its top open to constitute the said discharge orifice.

The interior space and the open base and top thereof are preferably free from obstructions to the flow of compressed air thereinto and to the flow of a mixture of a dose of fluent material present in the said interior space from the open top thereof.

In a first embodiment of the dispenser the above-mentioned obturator can be a slitted diaphragm, of elastic resilient material, whereby the slit of the diaphragm will open at a given excess pressure in the compression space of the piston pump.

In another embodiment of dispenser, the obturator can comprise a breakable diaphragm across the junction of the container inlet opening and the compressed air outlet of the piston pump and pin means mounted on the frontal face of the piston of the pump which pin means are adapted to rupture the diaphragm when the piston reaches a position near the end of its compression stroke.

In a third embodiment of the air pressure-operated dispenser according to the invention the obturator can comprise a flexible transverse wall member having an aperture therein, a plug member mounted detachably on the wall of the wall member surrounding the aperture thereof and obturating the latter in the non-dispensing position, and a pin member on the frontal face of the piston of the pump which pin member is adapted to abut the plug member and push the same out of the aperture when the piston reaches a determined position during its compression stroke.

Preferably, the volume of the interior space of the single dose container should be so proportioned in relation to the dimensions of the compression space in the air-compressing piston pump of the dispenser according to the invention that a single compression stroke of the piston is sufficient to expel the entire dose of fluent material out of the top opening of the interior space of the container, without leaving any residue of the liquid or powder material in the container.

In the case of the container and pump being integral, the dispenser will usually be thrown away after use. A pump bearing a separable container may be re-used after replacing an empty container by a full one.

The invention will now be described in greater detail in the following specification taken in connection with the accompanying drawings in which:

FIG. 1 is a side view of a first embodiment of a dispenser in accordance with the invention;

FIG. 2 is a longitudinal section of the air-compressing piston pump of the dispenser shown in FIG. 1, with the parts in the non-dispensing position;

FIG. 3 is a view of a second embodiment of a dispenser according to the invention, with the parts in the non-dispensing position and all of them except the piston in longitudinal section;

FIG. 4 is a view of the embodiment of FIG. 3 with the parts in the dispensing position;

Figure 5:
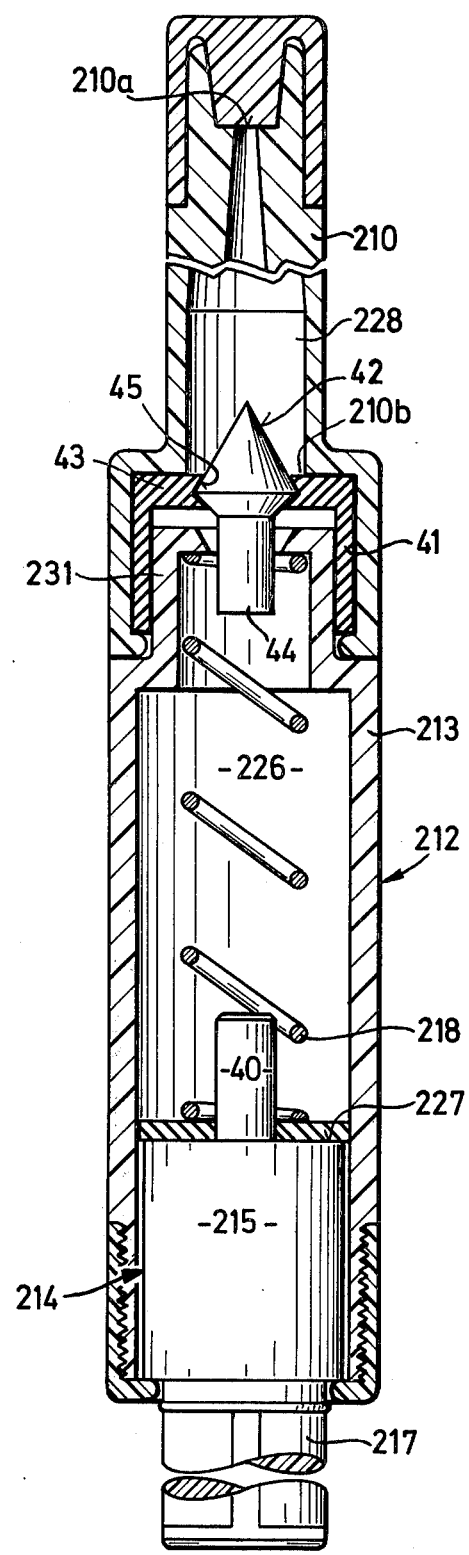
FIG. 5 is a view of a third embodiment of a dispenser according to the invention with the parts in the non-dispensing position and all of them except the piston in longitudinal section.

In the first embodiment of a dispenser according to the invention, shown in FIGS. 1 and 2, a container or cartridge 10 contains a single dose of product to be dispensed which product is in liquid or powder form. The hollow interior of cartridge 10 is of the same shape as that of chamber 128 inside cartridge portion 110 in the embodiment shown in FIGS. 3 and 4 or as that of chamber 228 inside cartridge portion 210 in the embodiment shown in FIGS. 5 and 5a. Cartridge 10 is operatively coupled, for instance snap-fitted, on a hollow stem member 11 constituting the junction means of an air-compressing piston pump 12 which comprises an outer cylinder 13 and a piston 14, a piston head 15 of which is slidably mounted in cylinder 13 and has a piston rod portion 17 thereof which protrudes from cylinder 13. The pump is operated by pressure, preferably with the thumb of one hand, exercized on the end of the piston rod portion 17, while two fingers of the same hand grip the cylinder by means of a gripping flange 16 which surrounds and is integral with cylinder 13. While a spring 18 urges the piston 14 out of the cylinder 13, an internal annular flange 13a about the open end of cylinder 13 prevents piston 14 from being removed entirely from cylinder 13. A gasket 19 seals the piston head 15 during its movement in the cylinder 13 against the internal wall of the latter.

The end wall 20 of cylinder 13 toward which piston head 15 moves during a compression stroke bears at its inside a diaphragm member 21 which is held in position against wall 20 by means of a retaining ring 22 having a central aperture 23 therein. Registering with aperture 23, the central duct 24 of hollow stem member 11 opens toward the compressed air inlet opening 10b of cartridge 10. Hollow stem member 11 is preferably centrally located on and integral with the end wall 20 of cylinder 13.

The diaphragm member 21 may be made of rubber or of thermoplastic or similar synthetic material and has preferably a substantially circular shape, conforming to the internal cross sectional area of cylinder 13, and has a slit 25 centrally located therein and extending therethrough. The diaphragm member 21 may be of uniform thickness or it may have a recessed central portion, thus requiring a slit of lesser diameter, as the lips of of the slit will be more readily flexible.

The slitted diaphragm member 21 prevents the passage of compressed air from the compression space 26 which is located in cylinder 13 between the diaphragm member 21 and retaining ring 22 on the one hand, and the frontal face 27 of piston head 15, on the other hand, until the pressure of the compressed air exceeds a determined value, at which time the slit 25 will open, allowing compressed air to pass through the diaphragm member 21. The limit of the aforesaid opening pressure is preferably chosen at such value that the slit 25 of diaphragm member 21 will not open until the frontal face 27 of piston head 15 approaches the diaphragm member 21 closely, toward the end of the compression stroke of piston 14.

The amount of pressure required to open the slit 25 is also dependent upon the diameter of aperture 23 in retaining ring 22, which aperture diameter must be chosen accordingly to attain the desired degree of compression.

Figure 7A:
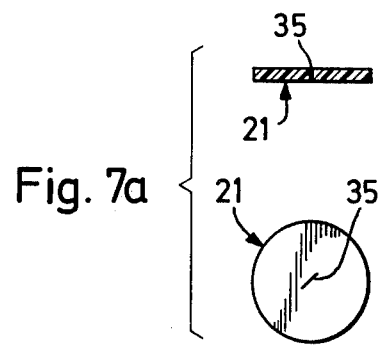
FIGS. 7(a) and 7(b) are each cross section and plan views of embodiments of a diaphragm member.
Figure 7B:
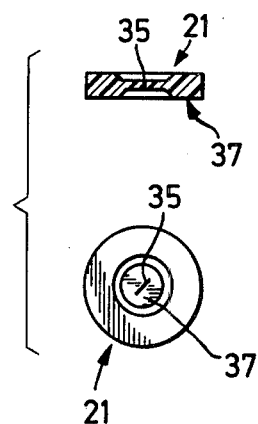

Referring now to FIGS. 7(a) and 7(b) two alternative embodiments of diaphragm member 21 are disclosed. The member may be constructed of rubber, plastic or the like and has a substantially annular shape, conforming to the cross section of the cylinder 14 and has a slit 35 centrally located and extending therethrough. In the embodiment of FIG. 7(a) the diaphragm has a uniform thickness while in the embodiment of FIG. 7(b) the device has a recessed central portion 37. Referring to FIG. 2, the diaphragm retainer 32 has a central aperture overlying the slit 35 in the diaphragm member.

The single dose container 10 may be made of thermoplastic material and preferably has a tapered free end portion 28, the top opening 10a of which can be closed during storage by a cap (not shown).

During compression, when the frontal face 27 of piston head 15 reaches the end of its stroke, the diaphragm slit 25 opens and a major portion of the air compressed in compression space 26 of cylinder 13 is suddenly released to flow through aperture 23 and outlet duct 24 into the single dose cartridge 10 set with its end having inlet opening 10b on stem portion 11, whereupon the air flow forces the full dose of fluent material contained in the hollow interior of cartridge 10 out of the latter in a spray of liquid droplets or fine powder particles.

The top end of duct 24 has preferably an outwardly tapered bevel face 29 toward the inlet opening 10*b* of cartridge 10 in order to avoid that residual product is left in the dead angle that may otherwise be formed in the latter opening if the open end of duct 24 forms a shoulder therein.

When empty, the cartridge 10 may be removed from step portion 11 of the pump and thrown away, and a new cartridge 10 may be snap-fitted or otherwise coupled to stem portion 11, in preparation for a subsequent dispensing operation. A cap (not shown) covering discharge orifice 10*a* must of course be removed before use of the dispenser. After dispensing, and upon release of piston rod 17, spring 18 returns piston 14 to its initial position shown in FIG. 2.

Referring now to FIG. 3, a second embodiment of a dispenser according to the invention is designed to be entirely disposed of after a single use in contrast to the embodiment of FIGS. 1 and 2. In this embodiment the product cartridge and the cylinder of the pump are combined in an integral cartridge cylinder assembly 30 rather than having a separate cartridge and cylinder. Furthermore, a perforating pin member 36 extends from the frontal piston face 127 toward the end wall 31 of the compression chamber 32. The length of this pin member 36 is chosen such that a breakable diaphragm 33 is ruptured by the pin member 36 as the piston 115 reaches the end of its compression stroke. The diaphragm 33 is seated within a stepped recess 34 of the cartridge portion 110 of the dispenser and is supported by a supporting sleeve 38 and is preferably integral with diaphragm 33. The construction of the supporting sleeve 38 is shown in detail in FIG. 6. In the non-dispensing position shown in FIG. 3, a cap 39 has been placed over the discharge orifice 110*a* of the cartridge portion 110.

The operation of the embodiment is substantially similar to that of the first described embodiment; compressed air builds up ahead of piston-face 127 as the piston 115 moves towards the diaphragm 33. As the piston 115 reaches the end of its compression stroke, perforator member 36 ruptures diaphragm 33, and the compressed air surges into the interior 128 of the cartridge portion 110, acting directly on the product and forcing the latter out of orifice 119*a*. No return spring need to be provided since the entire device is thrown away from a single use. FIG. 4 shows the device of FIG. 3 after the compression stroke has been completed. Perforator member 36 now extends through the ruptured diaphragm 33. The product has been dispensed through the discharge orifice 110 member, cap 39 having been previously removed.

FIG. 5 shows a third embodiment of the subject invention, in which the piston pump 212 and the cartridge 210 are separate members and the dispenser is reusable. A spring 218 is thus provided in this device, although it is obvious that the piston 214 could, alternatively, be withdrawn to its initial position by hand or by any other desired means. A probe member 40 is mounted on the piston face 227 and extends toward the diaphragm member 41, the flexible diaphragm 43 of which holds in closing position a plug 42 movably seated at the base opening 210*b* of the cartridge 210. The plug has a step portion 44 which extends into the cylinder 213 to a sufficient depth such that probe member 40 contacts the plug 42, at the end of the compression stroke of the cylinder, with sufficient force to drive the plug 42 from its seat in a central aperture 45 of diaphragm 43, into the interior 228 of cartridge portion 210, thereby allowing the compressed air from compression space 226 to pass suddenly into the product cartridge 210 and out of discharge orifice 210*a* of the latter. Empty cartridge 210 may then be removed and a new cartridge comprising inlet member 41 and plug 42 may be fitted over the cylinder in the manner as heretofore described. Spring 218 forces the piston 214 to return to its initial position once piston rod 217 is released, from which position the dispenser may again be activated. It will be apparent that the perforating member of FIG. 5 could be constructed to be interchangeably used with product dispensing cartridges of varying design.

Instead of having an annular groove provided in the wall surrounding the central aperture 45 of diaphragm 43, such a groove may also be provided about the circumference of plug 42, in a zone of the latter preferably at or adjacent its largest diameter portion.

The hollow interior of cartridge 210 is preferably not filled completely with the product dose to be dispensed, as, especially in the case of a dose of fine powder, this may lead to the charge acting as a solid wall and preventing the compressed air from moving plug 42 out of its seat in diaphragm 43. Normally, a fine powder dose may fill, e.g., one half or a third of the volume of the interior of cartridge 210.

The largest diameter of the plug 42 radially to the cylinder axis must be smaller than the diameter of the interior of cartridge 210 in the region of the latter adjacent diaphragm 43, so that compressed air may bypass the plug.

Figure 5A:
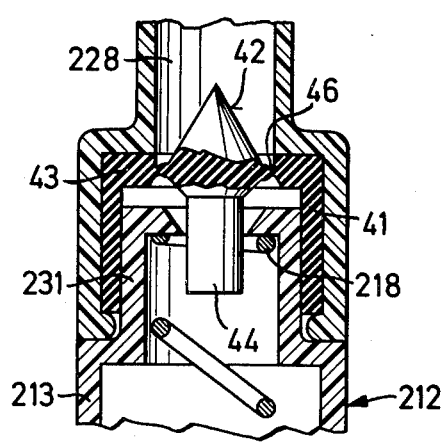
FIG. 5a is a partial sectional view of the middle position of an embodiment similar to that shown in FIG. 5.
Figure 6:
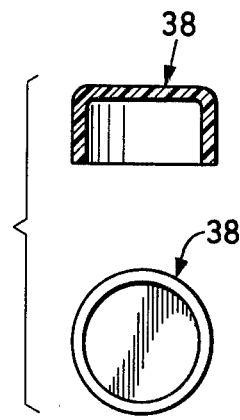
FIG. 6 is a cross section and plan view of an embodiment of a diaphragm retainer.

In the modification of this embodiment shown in FIG. 5a, the diaphragm 43 and the plug 42 are manufactured in one piece, a thin peripheral annular membrane portion 46 being provided to connect the two elements. Membrane portion 46 is easily ruptured when probe member 40 hits stem portion 44 of plug 42.

The interior surface of the chamber inside cartridges 10, 110 or 210 is tapered toward the discharge orifice 10a, 110a or 210a at least in the region of the chamber (128, 228) adjacent that orifice.

The cross-sectional area of the inlet openings 10b, 110b, 210b of that chamber at the base of cartridges 10, 110 or 210 should be of a diameter smaller than or equal to the width of the opening in the adjacent end wall 20, 31 or 231 of the cylinder of the piston pump, thereby ensuring that the entire dose or practically the entire dose of liquid or pulverulent product will be expelled from the cartridge. The volume of the cylinder of the piston pump must be of adequate size and preferably much larger than the chamber in the cartridge containing the product.

What we claim is:

1. An air pressure-operated dispenser for spraying a single dose of a fluent material or liquid or powder form, and comprising:
   a. a single dose container having a compressed air inlet opening and a closable discharge orifice, the interior space and the inlet opening and the discharge orifice thereof being free from obstructions to the flow of compressed air thereinto and to flow of a mixture of a dose of fluent material present in the interior space from the discharge orifice thereof;
   b. means for closing the discharge orifice in a non-dispensing position of the dispenser;
   c. an air-compressing piston pump having a compressed air outlet from a compression space thereof; and
   d. value means for releasing a flow of compressed air after build-up of a determined excess pressure, the inlet opening of the single dose container being joined to the compressed air outlet of the compression space and wherein the valve means comprise an obturator located at the junction of the inlet opening and the compressed air outlet, the obturator being a breakable diaphragm across the junction, and pin means mounted on the frontal face of the piston of the pump adapted to rupture the diaphragm when the piston reaches a position near the end of its compression stroke.

2. An air pressure-operated dispenser according to claim 1 wherein the compressed air outlet has the same configuration and diameter as the inlet opening.

3. An air pressure-operated dispenser according to claim 1 wherein the single dose container is separately mounted on the piston pump.

4. An air pressure-operated dispenser according to claim 1 wherein the single dose container and the piston pump have a common housing.

5. An air pressure-operated dispenser according to claim 4 wherein the housing constitutes the cylinder of the piston pump.

6. An air pressure-operated dispenser according to claim 5 wherein the housing constitutes the wall of the container.

7. An air pressure-operated dispenser according to claim 1 wherein part of the interior space of the container is of frustoconical shape having an open base constituting the compressed air inlet opening and an open top constituting the discharge orifice.

8. An air pressure-operated dispenser according to claim 1 wherein the obturator comprises a flexible transverse wall member having an aperture therein, a plug member mounted detachably in the wall of the wall member surrounding the aperture and obturating the latter in non-dispensing position, and a pin member on the frontal face of the piston of the pump adapted to abut the plug member and push the same out of the aperture when the piston reaches a determined position during its compression stroke.

9. An air pressure-operated dispenser according to claim 1 wherein the volume of the interior space of the container and the compression space of said air-compressing piston pump are so dimensioned that a single compression stroke of the piston of the pump is sufficient to expel an entire dose of fluent material located in the interior space out of the top opening of the interior space.

* * * * *

UNITED STATES PATENT OFFICE
CERTIFICATE OF CORRECTION

Patent No. 4,017,007          Dated April 12, 1977

Inventor(s) Pasquale R. Riccio

It is certified that error appears in the above-identified patent and that said Letters Patent are hereby corrected as shown below:

Column 6, line 41, "orifice 119a" should read
-- orifice 110a --.

Column 7, Claim 1, line 2, " a fluent material or liquid or powder form" should read -- a fluent material of liquid or powder form --.

Signed and Sealed this

Twenty-seventh Day of September 1977

[SEAL]

Attest:

RUTH C. MASON
*Attesting Officer*

LUTRELLE F. PARKER
*Acting Commissioner of Patents and Trademarks*